(12) United States Patent
Yao

(10) Patent No.: US 9,068,923 B2
(45) Date of Patent: *Jun. 30, 2015

(54) METHOD FOR FABRICATING CARBON NANOTUBE ARRAY SENSOR

(75) Inventor: Yuan Yao, Beijing (CN)

(73) Assignees: Tsinghua University, Beijing (CN); HON HAI PRECISION INDUSTRY CO., LTD., New Taipei (TW)

(*) Notice: Subject to any disclaimer, the term of this patent is extended or adjusted under 35 U.S.C. 154(b) by 502 days.

This patent is subject to a terminal disclaimer.

(21) Appl. No.: 12/732,123

(22) Filed: Mar. 25, 2010

(65) Prior Publication Data

US 2010/0216273 A1  Aug. 26, 2010

Related U.S. Application Data

(63) Continuation of application No. 12/570,621, filed on Sep. 30, 2009.

(30) Foreign Application Priority Data

Feb. 20, 2009 (CN) .......................... 2009 1 0105489

(51) Int. Cl.
*H01L 21/00* (2006.01)
*G01N 27/12* (2006.01)
*G01N 27/414* (2006.01)

(52) U.S. Cl.
CPC ............ *G01N 27/127* (2013.01); *G01N 27/414* (2013.01)

(58) Field of Classification Search
CPC . G01N 27/414; B32Y 30/00; H01L 21/32051
USPC ...................... 438/49; 977/742; 257/E21.295
See application file for complete search history.

(56) References Cited

U.S. PATENT DOCUMENTS 6,232,706 B1 * 5/2001 Dai et al. ...................... 313/309
7,736,615 B2 * 6/2010 Kawabata et al. .......... 423/447.2
(Continued)

FOREIGN PATENT DOCUMENTS

CN 101252145 A 8/2008
CN 101281154    10/2008
(Continued)

OTHER PUBLICATIONS

Sumio Iijima, Helical microtubules of graphitic carbon, 1991, p. 56-58, vol. 354, Nature.
(Continued)

*Primary Examiner* — Fernando L Toledo
*Assistant Examiner* — Neil Prasad
(74) *Attorney, Agent, or Firm* — Novak Druce Connolly Bove + Quigg LLP

(57) ABSTRACT

A method of fabricating a carbon nanotube array sensor includes the following steps. A carbon nanotube array, a first electrode and a second electrode are provided, the carbon nanotube array includes a plurality of carbon nanotubes. Each of the carbon nanotubes includes a first end and a second end opposite to the first end. A first metallophilic layer is formed on the first end of each of the carbon nanotubes. At least one first conductive metal layer is arranged between the first metallophilic layer and the first electrode to electrically connect each of the carbon nanotubes with the first electrode. A second metallophilic layer is formed on the second end of each of the carbon nanotubes. At least one second conductive metal layer is arranged between the second metallophilic layer and the second electrode to electrically connect each of the carbon nanotubes with the second electrode.

14 Claims, 15 Drawing Sheets

(56) References Cited

U.S. PATENT DOCUMENTS

| | | |
|---|---|---|
| 2006/0169585 A1 | 8/2006 | Nagahara et al. |
| 2006/0290343 A1* | 12/2006 | Crafts et al. ............... 324/158.1 |
| 2007/0148963 A1* | 6/2007 | Chan et al. .................... 438/637 |
| 2008/0017981 A1 | 1/2008 | Yaniv |
| 2009/0091343 A1* | 4/2009 | Wu et al. ....................... 324/754 |
| 2009/0256258 A1* | 10/2009 | Kreupl et al. ................. 257/741 |
| 2010/0213954 A1* | 8/2010 | Yao ............................... 324/691 |

FOREIGN PATENT DOCUMENTS

| | | |
|---|---|---|
| CN | 101281154 A | 10/2008 |
| JP | 2002100280 | 4/2002 |
| JP | 2003286017 | 10/2003 |
| JP | 2004528727 | 9/2004 |
| JP | 2006112819 | 4/2006 |
| JP | 2007093294 | 4/2007 |
| WO | WO2009101664 | 8/2009 |

OTHER PUBLICATIONS

Ting Zhang et al., Recent progress in carbon nanotube-based gas sensors, 2008, vol. 19, 332001, Nanotechnology.

* cited by examiner

METHOD FOR FABRICATING CARBON NANOTUBE ARRAY SENSOR

This application claims all benefits accruing under 35 U.S.C. §119 from China Patent Application No. 200910105489.8, filed on Feb. 20, 2009, in the China Intellectual Property Office. This application is a continuation application of U.S. patent application Ser. No. 12/570,621, filed Sep. 30, 2009, entitled, "carbon nanotube array sensor".

BACKGROUND

1. Technical Field

The present disclosure relates to sensors, and in particular, relates to a method for fabricating carbon nanotube array sensor.

2. Description of the Related Art

Carbon nanotubes can function as either a conductor, like metal, or a semiconductor, according to the rolled shape and the diameter of the helical tubes. With metallic-like nanotubes, it has been found that a one-dimensional carbon-based structure can conduct a current at room temperature with essentially no resistance. Further, electrons can be considered as moving freely through the structure, so that metallic-like nanotubes can be used as ideal interconnects. When semiconductor nanotubes are connected to two metal electrodes, the structure can function as a field effect transistor, wherein the nanotubes can be switched from a conducting to an insulating state by applying a voltage to a gate electrode. Therefore, carbon nanotubes are potential building blocks for nanoelectronic devices because of their unique structural, physical, and chemical properties.

Carbon nanotubes have been shown to be a highly sensitive chemical and biological sensor. The utility of detecting the presence or absence of a specific agent is one type of known detection scheme. As the agent attaches itself to a carbon nanotube, the measurable resistance of the nanotube changes. As the resistance changes, a quantitative result, e.g., concentration may be determined. Known nanotube systems use a single nanotube (only one path for determining resistance), a parallel array of nanotubes, or a network array of nanotubes to determine the presence of an unwanted agent. A conventional carbon nanotube array sensor includes a carbon nanotube array and two electrodes respectively disposed opposite ends of the carbon nanotube array along a longitudinal axis thereof. In a method of making the carbon nanotube array sensor, the carbon nanotube array is directly adhered on surfaces of the two electrodes via gold slurry.

However, the gold slurry is conductive material and includes insulative solvent and binder besides gold particles. Therefore, conductive capacity between the carbon nanotube array and the two electrodes can be decreased. Furthermore, the carbon nanotube array has no firm connection to the two electrodes because of bad wettability between the gold slurry and the carbon nanotube array, thereby decreasing sensitivity and precision of the carbon nanotube array sensor.

What is needed, therefore, is a carbon nanotube array sensor and a method for fabricating the same, which can overcome the above-described shortcomings.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
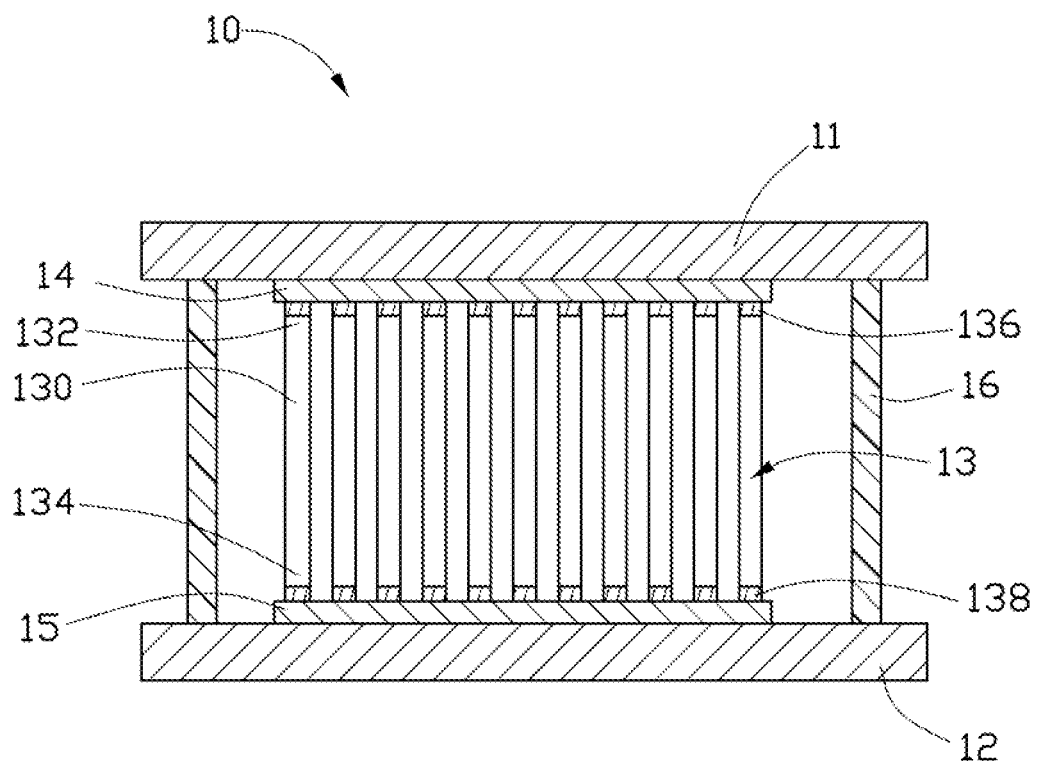
FIG. 1 is a schematic, cross-sectional view of an embodiment of a carbon nanotube array sensor.
Figure 2:
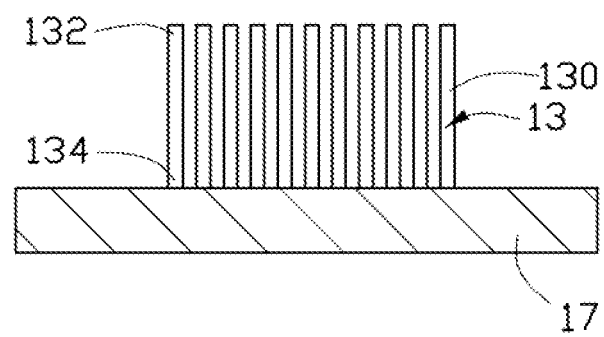
FIGS. 2 to 7 are sectional views of fabricating a carbon nanotube array sensor of FIG. 1.
Figure 3:
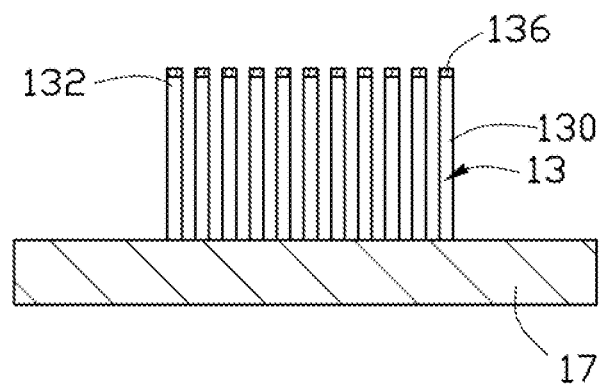
Figure 4:
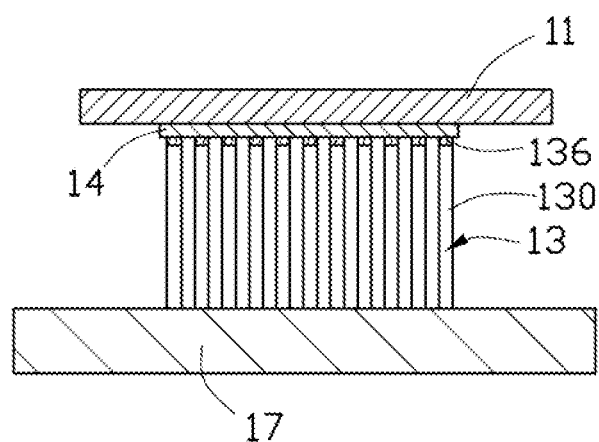
Figure 5:
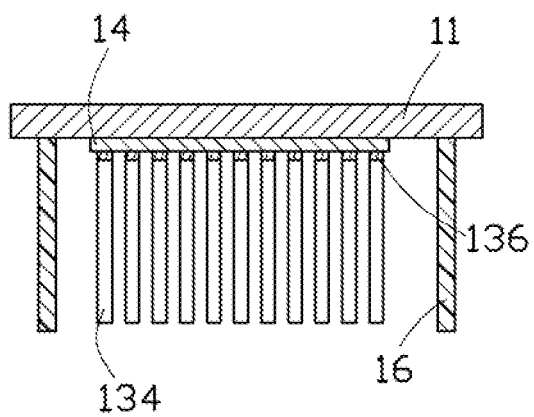
Figure 6:
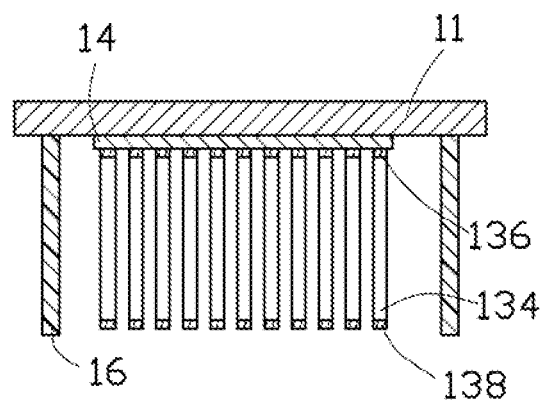
Figure 7:
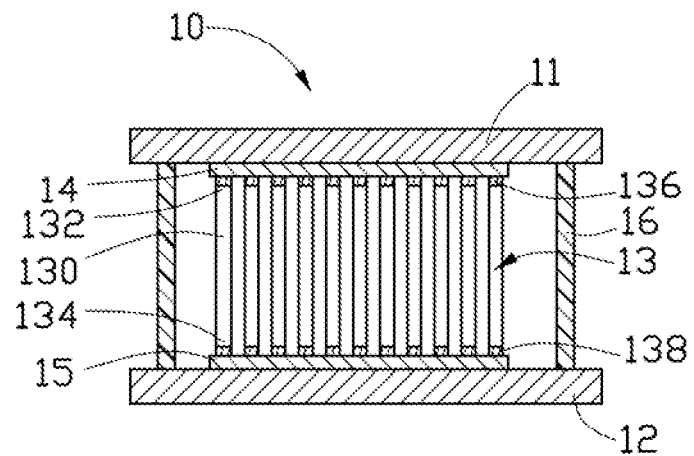
Figure 8:
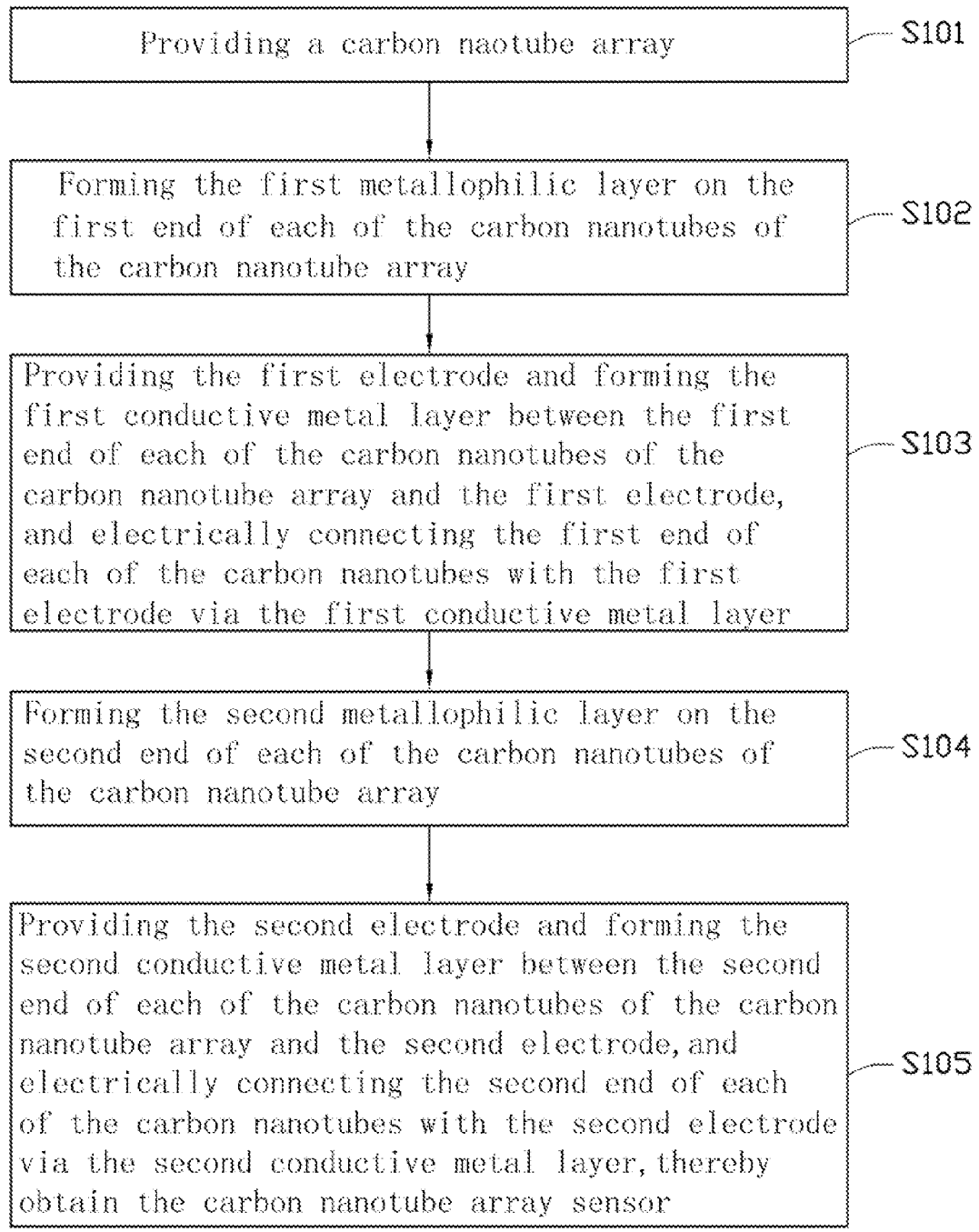
FIG. 8 is a flow chart of a method for manufacturing a carbon nanotube array sensor.

Referring to the embodiment shown FIG. 1, a carbon nanotube array sensor 10 includes a first electrode 11, a second electrode 12, a carbon nanotube array 13, a first conductive metal layer 14, and a second conductive metal layer 15. The carbon nanotube array 13 is located between the first and second electrodes 11, 12. The first conductive metal layer 14 is disposed between the first electrode 11 and the carbon nanotube array 13. The second conductive layer 15 is interposed between the second electrode 12 and the carbon nanotube array 13.

The first and second electrodes 11, 12 are spaced apart from each other and are made of conductive material, such as copper, aluminum, gold, silver, iron, alloys thereof, or the like. In one embodiment, the first and second electrodes 11, 12 are made of copper and have thicknesses of about 1 micron (μm) to about 20 μm.

The carbon nanotube array 13 includes a number of carbon nanotubes 130 arrange substantially along the same direction. Each of the carbon nanotubes 130 has approximately the same length and includes a first end 132, a second end 134, a first metallophilic layer 136, and a second metallophilic layer 138. The second end 134 is opposite to the first end 132 along longitudinal axes of the carbon nanotubes 130. The first metallophilic layer 136 is disposed around a surface of the first end 132. The second metallophilic layer 138 is disposed around a surface of the second end 134. The first end 132 of the carbon nanotubes 130 is electrically connected to the first electrode 11 via the first metallophilic layer 136. The second end 134 of the carbon nanotubes 130 is electrically connected to the second electrode 12 via the second metallophilic layer 138.

In one embodiment, the carbon nanotube array can be obtained via chemical vapor deposition or other conventional methods. The carbon nanotubes 130 may be single-walled carbon nanotubes, double-walled carbon nanotubes, multi-walled carbon nanotubes, or their combinations. The single-walled carbon nanotube has a diameter of about 0.5 nanometers (nm) to about 50 nm. The double-walled carbon nanotube has a diameter of about 1.0 nm to about 50 nm. The multi-walled carbon nanotube has a diameter of about 1.5 nm to about 50 nm. In one embodiment, the carbon nanotubes 130 are multi-walled carbon nanotubes and have thickness of about 1 μm to about 800 μm.

The first and second metallophilic layers 136, 138 may be deposited on the first and second ends 132, 134 of the carbon nanotube array 13 via a process, such as electroplating, electroless plating, evaporating plating, magnetron sputtering, or the like. The first metallophilic layer 136 entirely or in part coats the first ends 132 of the carbon nanotubes 130. The second metallophilic layer 138 entirely or in part coats the second ends 134 of the carbon nanotubes 130. The carbon nanotubes 130 can be firmly affixed with and electrically connected to the first and second conductive metal layers 14, 15 because there are good wettability between the first and second metallophilic layers 136, 138 and the carbon nanotubes 130, and between the first and second metallophilic layers 136, 138 and the first and second conductive metal layers 14, 15. The first and second metallophilic layers 136, 138 may be made of palladium, chromium, nickel, titanium, magnesium, alloys thereof, or the like, and have thicknesses of about 0.5 nm to about 50 nm.

The first conductive metal layer 14 is disposed on a surface of the first electrode 11. The second conductive metal layer 15 is disposed on a surface of the second electrode 12. Further, the first ends 132 having the first metallophilic layer 136 can be entirely or in partially embed into the first conductive metal layer 14. The second ends 134 having the second metallophilic layer 138 can be entirely or in partially embed into the second conductive metal layer 15. Thereby, the first and second metallophilic layers 136, 138 are electrically connected with the first and second conductive metal layers 14, 15 and electrically connect the carbon nanotube array 13 with the first and second electrodes 11, 12.

When the first and second conductive metal layers 14, 15 are heated to a viscous state, they should have good wettability with the first and second electrodes 11, 12. The first and second conductive metal layers 14, 15 may be made of metal having a low melting-point, such as indium, stanuum, copper, plumbum, stibium, gold, siliver, alloy thereof, or the like. Furthermore, the first and second conductive metal layers 14, 15 can have melting-point lower than the first and second electrodes 11, 12, thereby preventing the first and second electrodes 11, 12 from melting when the first and second conductive metal layers 14, 15 are heated. The first and second metallophilic layers 136, 138 can firmly conjunct with the first and second electrodes 11, 12. Because there are good wettability between the first and second conductive metal layers 14, 15 and the first and second electrodes 11, 12, and there are good wettability between the first and second conductive metal layers 14, 15 and the first and second metallophilic layers 136, 138.

In one embodiment, the carbon nanotube array sensor 10 further includes a supporter 16. The supporter 16 is disposed between the first and second electrodes 11, 12. The supporter 16 is used to space the first and second electrodes 11, 12 for preventing the carbon nanotube array 13 from damaging or bending, thereby prolonging the lifespan of the carbon nanotube array sensor 10. The supporter 16 may be made of insulating material, such as glass, ceramic, or the like.

Furthermore, in one embodiment, the carbon nanotube array sensor 10 may includes a modified layer (not shown). The modified layer is a coating disposed on an outer surface of each of the carbon nanotubes 130 and used to improve the sensitivity and precision of the carbon nanotube array sensor 10. The modified layer may be made of palladium, platinum, gold, or the like. The different modified layer, which is made of different material, may have different function. For example, the modified layer made of palladium can improve the precision of the carbon nanotube array sensor 10 to measure content of hydrogen and methane. Methods for making the modified layer include electroplating, electroless plating, evaporating plating, magnetron sputtering, or the like.

Referring to FIGS. 2-7 and FIG. 8, a method for fabricating the carbon nanotube array sensor 10 is shown. The method includes the following steps such as from S10 to S50.

Step S10: providing a carbon nanotube array 13. The carbon nanotube array 13 includes a plurality of the carbon nanotubes 130. Each of the carbon nanotubes 130 includes the first end 132 and the second end 134. The carbon nanotubes 130 may be single-walled carbon nanotubes, double-walled carbon nanotubes, multi-walled carbon nanotubes, or their combinations. The carbon nanotube array 13 can be a super-aligned carbon nanotube array. In one embodiment, the super-aligned carbon nanotube array is made by chemical vapor deposition process. The chemical vapor deposition process includes the following steps such as from S11 to S15.

Step S11: providing a substantially flat and smooth substrate 17. The substrate 17 may be a P-type silicon substrate, a N-type silicon substrate, or a silicon substrate having oxide layer disposed thereon. In one embodiment, the substrate 17 is a P-type silicon substrate having a width of about 4 inches.

Step S12: forming a catalyst on the substrate 17. The catalyst can be made of iron (Fe), cobalt (Co), nickel (Ni), or any combination alloy thereof.

Step S13: annealing the substrate with the catalyst at a temperature in the range of about 700° C. to about 900° C. in air for about 30 minutes to about 90 minutes.

Step S14: heating the substrate 17 with the catalyst at a temperature in the approximate range from about 500° C. to about 740° C. in a furnace with a protective gas therein.

Step S15: supplying a carbon source gas to the furnace for about 5 minutes to about 30 minutes and growing a super-aligned carbon nanotube array 13. The carbon source gas may be hydrocarbon gas, such as ethylene ($C_2H_4$), methane ($CH_4$), acetylene ($C_2H_2$), ethane ($C_2H_6$), or any combination thereof. The protective gas may be nitrogen or inert gases. In one embodiment, the carbon source gas is acetylene, and the inert gas is argon. The obtained carbon nanotube array 13 is substantially free of impurities, such as residual catalyst particle or amorphous carbon by controlling the growing conditions of the chemical vapor deposition. The carbon nanotubes 130 of the carbon nanotube array 13 are attracted to each other by van der Waals force. Furthermore, the carbon nanotube array sensor 10 can be made from any suitable carbon nanotube array.

Step S20: forming the first metallophilic layer 136 on the first ends 132 of the carbon nanotubes 130. The first metallophilic layer 136 may be deposited on the first ends 132 of the carbon nanotube array 13 via a process, such as electroplating, electroless plating, evaporating plating, magnetron sputtering, or the like. In one embodiment, the first metallophilic layer 136 is deposited on the first end 132 via electroplating process. The electroplating process includes the following steps such as from S21 to S25.

Step S21: immersing the first ends 132 of the carbon nanotubes 130 into an acid solution to acidize it so that the residual, such as catalyst particles, on a surface of the first ends 132 can be removed. The acid solution may be sulfuric acid, hydrochloric acid, nitric acid, or the like, or their combinations. In one embodiment, a mixture of the sulfuric acid and the nitric acid is employed and a weight ratio of the sulfuric acid and the nitric acid is about 3:1.

Step S22: providing an electroplating solution. The electroplating solution includes a metal salt. The metal salt may be magnesium sulfate, palladium chloride, chromium sulfate, or the like.

Step S23: immersing the treated first ends 132 of the carbon nanotubes 130 into the electroplating solution, wherein the treated first ends 132 are function as a cathode. An anode is immersed into the electroplating solution.

Step S24: applying a predetermined voltage between the first ends 132 and the anode to form the first metallophilic layer 136 on the first ends 132. In one embodiment the voltage is applied for about 5 to about 10 minutes.

Step S25: drying the electroplated first metallophilic layer 136.

In above electroplating process, the anode may be made of some material which has a lower chemical activity than the first metallophilic layer 136 or is the same as the material of the first metallophilic layer 136. The material may be gold, graphite, palladium, nickel, rhodium, magnesium, titanium, chromium, or the like. In one embodiment, the anode is made of material same as that of the first metallophilic layer 136, such as palladium, thereby contributing metal ions to the electroplating solution when the metal ions of the electroplating solution are exhausted, because metal ions of the anode can be dissolved in the electroplating solution when some metal ions has been plated on the first ends 132. In one embodiment, a weight ratio of the palladium chloride in the electroplating solution ranges from about 20% to about 35%. A solvent in the electroplating solution may be water. The electroplating solution has a PH value of about 3.5 to about 6. A current applied to the first ends 132 is a direct current and has a current density of about 5 milliamperes per square centimeter to about 10 milliamperes per square centimeter. In one embodiment, the electroplating solution may further include a conductive salt solution, such as ammonium chloride, thereby further improving conductivity of the electroplating solution. A weight ratio of the ammonium chloride in the electroplating solution may be about 3%.

Furthermore, the electroplating solution may include a buffer agent. In the electroplating process, hydrogen can be separated out from the cathode, thereby resulting in an increase of the PH value of the electroplating solution. The buffer agent can be used to stabilize the PH value of the electroplating solution. The buffer agent can also advantageously improve the scatting capability of the electroplating solution and stability of the first metallophilic layer 136.

Step S30: providing the first electrode 11 and forming the first conductive metal layer 14 between the first ends 132 of the carbon nanotubes 130 of the carbon nanotube array 13 and the first electrode 11, and electrically connecting the first ends 132 of the carbon nanotubes 130 with the first electrode 11 via the first conductive metal layer 14.

The electrically connecting process include the following steps such as from S31 to S33.

Step S31: providing the first electrode 11. A thickness of the first electrode 11 can range from about 1 μm to about 20 μm. The first electrode 11 may be made of copper, aluminum, iron, gold, silver, or the like. In one embodiment, the first electrode 11 is made of copper.

Step S32: forming the first conductive metal layer 14 between the first ends 132 of the carbon nanotubes 130 of the carbon nanotube array 13. The first conductive metal layer 14 may be made of indium, stannum, copper, plumbum, stibium, gold, silver, alloys thereof, or the like. As described above, the melting-point of the first conductive metal layer 14 can be lower than that of the first electrode 11. In one embodiment, the first conductive metal layer 14 is formed on a surface of the first electrode 11 via magnetron sputtering process, physical deposition, chemical vapor deposition, or the like.

Step S33: applying heat to the first conductive metal layer 14, and fixing the first ends 132 of the carbon nanotubes 130 on the first conductive metal layer 14, thereby electrically connecting the carbon nanotube array 13 with the first electrode 11. Applying heat to the first conductive metal layer 14 can be done by heating to the carbon nanotube array 13, the first conductive metal layer 14, the first electrode 11 or a combination thereof. The first ends 132 of the carbon nanotubes 130 can be inserted into the soften and/or melted first conductive metal layer 14. Furthermore, the first ends 132 of the carbon nanotubes 130 will be secured to the first conductive metal layer 14 when the first conductive metal layer 14 is cooled. The first ends 132 of the carbon nanotubes 130 can be entirely embedded into the soften first conductive metal layer 14. After cooling the soften first conductive metal layer 14, the carbon nanotube array 13 is firmly fixed on the first electrode 11. There is good wettability between the carbon nanotubes 130 and the first metallophilic layer 136, and between the first metallophilic layer 136 and the first conductive metal layer 14. Thus, the carbon nanotube array 13 can be firmly fixed to the first electrode 11 via the first conductive metal layer 14. The coupling of the first electrode 11 and the carbon nanotube array 13 is strong and will prevent the carbon nanotube array 13 from dislodging from the first electrode 11. This will improve the stability of the carbon nanotube array sensor 10.

Step S40: forming the second metallophilic layer 138 on the second ends 134 of the carbon nanotubes 130 of the carbon nanotube array 13. Before forming the second metallophilic layer 138, the substrate 17 should be firstly stripped from the carbon nanotube array 13. Since the first ends 132 of the carbon nanotubes 130 has been firmly fixed on the first electrode 11 and the binding force between the carbon nanotube array 13 and the substrate 17 is weak, the carbon nanotube array 13 can be easily stripped from the substrate 17 and may not be damaged. The steps of forming the second metallophilic layer 138 are similar to that of forming the first metallophilic layer 136.

Before forming the second metallophilic layer 138, an optional step of forming the supporter 16 may be performed. The supporter 16 can be adhered on the first electrode 100 via adhesive. The supporter 16 is made of insulative material, such as glass, ceramic, or the like.

Step S50: providing the second electrode 12 and forming the second conductive metal layer 15 between the second ends 134 of the carbon nanotubes 130 of the carbon nanotube array 13 and the second electrode 12, and electrically connecting the second ends 134 of the carbon nanotubes 130 with the second electrode 12 via the second conductive metal layer 15, thereby obtaining the carbon nanotube array sensor 10. The process of forming the second conductive metal layer 15 is similar to that of forming the first conductive metal layer 14.

The step S50 further includes a step of adhering the supporter 16 on the second electrode 12, thereby firmly fixing the supporter 16 between the first and second electrodes 11, 12. In one embodiment, one end of the supporter 16 can be adhered to the softened first conductive metal layer 14 in step S30, and the other end of the supporter 16 can be adhered by to the softened second conductive metal layer 14 in step S50. Alternatively, the supporter 16 can be adhered between the first and second electrodes 11, 12 by an adhesive.

The method may further include a step of forming a modified layer on the surface of the carbon nanotube array 130. The modified layer is used to improve the sensitivity and precision of the carbon nanotube array sensor 10. The modified layer may be made of palladium, platinum, gold, or the like. The different modified layers, which are made of different materials, may have different functions. For example, the modified layer made of palladium can improve the precision of the carbon nanotube array sensor 10 to measure content of hydrogen and methane.

The first and second conductive metal layers 14, 15 also can be formed on the two ends of the carbon nanotube array 13 via electroplating, chemical plating, magnetron sputtering, or the like.

The carbon nanotube array 13 of the carbon nanotube array sensor 10 functions as electron wire and when a current is applied to the carbon nanotubes 130 of the carbon nanotube array 13, an electrical conductivity between the first and second electrodes 11, 12 can be measured. Further, electron feature of the carbon nanotubes 130 depends on atom structure thereof, and when gas molecules are absorbed on surfaces of the carbon nanotubes 130, the atom structure of the carbon nanotubes 130 may be changed, the change scope can be measured according to the variation of the current. Furthermore, according to variation of quantity of gas molecules absorbed on the carbon nanotubes 130, the change scope of the current is different. Therefore, the carbon nanotube array sensor 10 can be used to measure the concentration of gas molecules. Moreover, difference of molecule structure and molecule weight of different gas molecules, which results in different change scope of atom structure of the carbon nanotubes 130. Therefore, the change scope of the current is different. As such, the carbon nanotube array sensor 10 also can be used to measure type of gas molecules.

Figure 9:
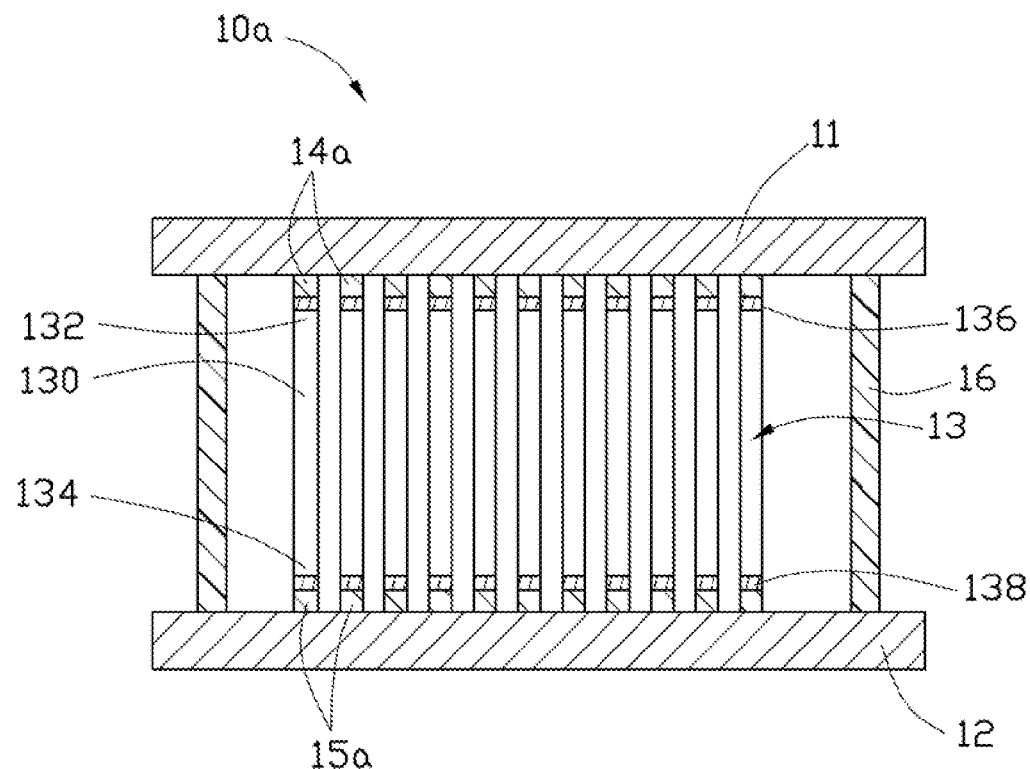
FIG. 9 is schematic, cross-sectional view of one embodiment of a carbon nanotube array sensor.
Figure 10:
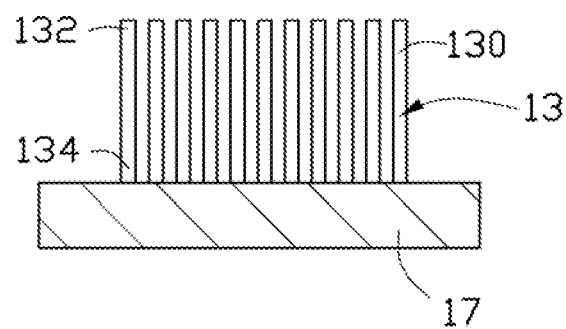
FIGS. 10 to 15 are sectional views of fabricating a carbon nanotube array sensor.
Figure 11:
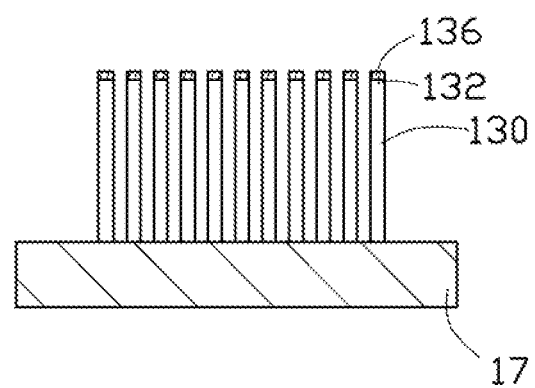
Figure 12:
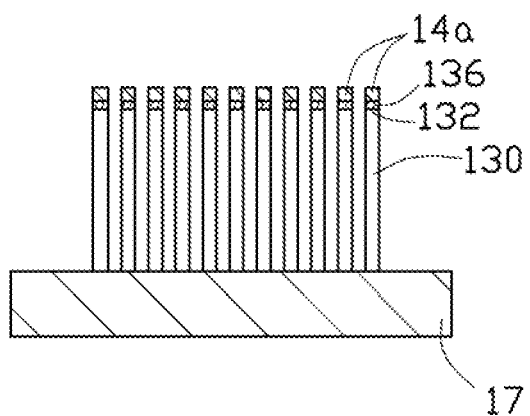
Figure 13:
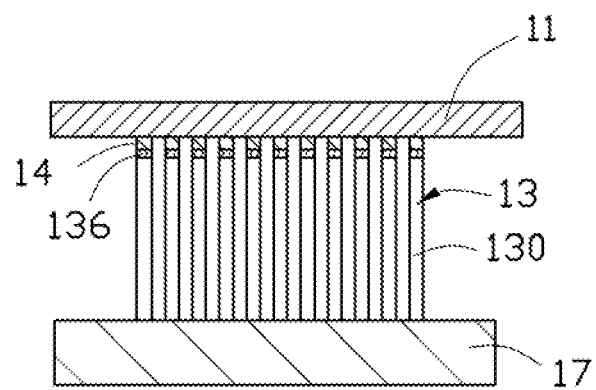
Figure 14:
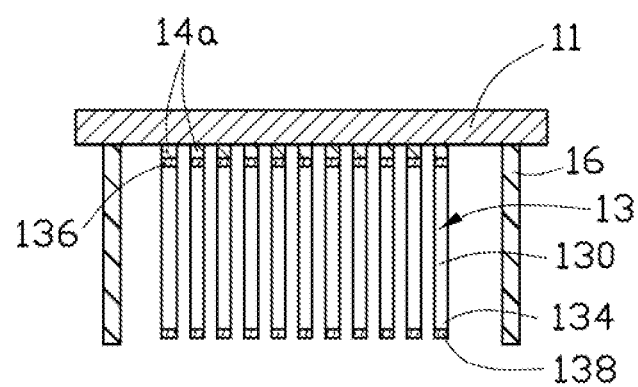
Figure 15:
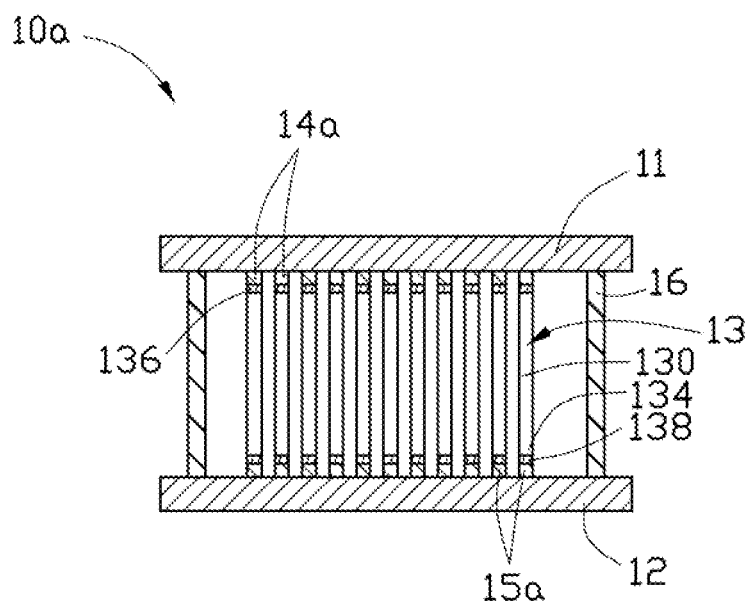

Referring to FIG. 9, one embodiment of a carbon nanotube array sensor 10a is shown. The carbon nanotube array sensor 10a is similar to the carbon nanotube array sensor 10 except that the carbon nanotube array sensor 10a includes a number of first conductive metal layers 14a and a number of second conductive metal layers 15a. The first conductive metal layers 14a are disposed between the first ends 132 of the carbon nanotubes 130 of the carbon nanotube array 13 and the first electrode 11. The second conductive metal layers 14a are located between the second ends 134 of the carbon nanotubes 130 of the carbon nanotube array 13 and the second electrode 12.

Referring to FIGS. 10-15, a process of fabricating the carbon nanotube array sensor 10a is shown. The process includes:

step S10a: providing the carbon nanotube array 13, each of the carbon nanotubes 130 of the carbon nanotube array 13 includes the first end 132 and the second end 134;

step S20a: forming the first metallophilic layer 136 on the first ends 132 of the carbon nanotubes 130;

step S30a: providing the first electrode 11 and forming a number of the first conductive metal layers 14a between the first electrode 11 and the first ends 132 of the carbon nanotubes 130 to electrically connect the first end 132 with the first electrode 11;

step S40a: forming the second metallophilic layer 138 on the second ends 134 of the carbon nanotubes 130; and step S50a: providing the second electrode 12 and forming a number of the second conductive metal layers 15a between the second electrode 12 and the second ends 134 of the carbon nanotubes 130 to electrically connect the second ends 134 with the second electrode 12.

In one embodiment, a number of the first conductive metal layers 14a are formed on the first ends 132. A number of the second conductive metal layers 15a are formed on the second ends 134. The first metallophilic layer 136 is embedded into the at least one first conductive metal layers 14a, and the second metallophilic layer 138 is embedded into the at least one second conductive metal layers 15a. A number of the first conductive metal layers 14a can be formed between the first electrode 11 and the first ends 132 of the carbon nanotubes 130 via chemical platting, electroplating, magnetron sputtering, or the like. A number of the second conductive metal layers 15a also can be formed between the second electrode 12 and the second ends 134 of the carbon nanotubes 130 via chemical platting, electroplating, magnetron sputtering, or the like.

This eliminates the need to employ conductive slurry, such as gold slurry, to electrically connect the carbon nanotube and the first and second electrodes because there is bad wettability between the gold slurry and the carbon nanotube array. The first metallophilic layer is deposited on the first end of the carbon nanotube, and the second metallophilic layer is deposited on the second end of the carbon nanotube. There is good wettiability not only between the first and second metallophilic layers and the carbon nanotube array, but also between the first and second metallophilic layers and the first and second conductive metal layers. Thus, the carbon nanotube array can be firmly fixed between and coupled to the first and second electrodes. Therefore, the sensitivity and precision of the carbon nanotube array sensor can be improved, and the life span of the carbon nanotube array sensor can be further prolonged.

It is to be understood, however, that even though numerous characteristics and advantages of the present embodiments have been set forth in the foregoing description, together with details of the structures and functions of the embodiments, the disclosure is illustrative only, and changes may be made in detail, especially in matters of shape, size, and arrangement of parts within the principles of the disclosure to the full extent indicated by the broad general meaning of the terms in which the appended claims are expressed.

It is also to be understood that the above description and the claims drawn to a method may include some indication in reference to certain steps. However, the indication used is only to be viewed for identification purposes and not as a suggestion as to an order for the steps.

What is claimed is:

1. A method for fabricating a carbon nanotube array sensor, the method comprising the following steps:
    providing a first electrode, a second electrode, and a carbon nanotube array, the carbon nanotube array comprising a plurality of carbon nanotubes, each of the carbon nanotubes comprising a first end and a second end opposite to the first end, the first and the second ends being arranged along a longitudinal axis of each of the carbon nanotubes;
    forming a first metallophilic layer and a second metallophilic layer, wherein the first metallophilic layer is located on the first end of each of the carbon nanotubes, and the second metallophilic layer is located on the second end of each of the carbon nanotubes;
    applying at least one first conductive metal layer between the first metallophilic layer and the first electrode, and at least one second conductive metal layer between the second metallophilic layer and the second electrode; and
    electrically connecting each of the carbon nanotubes with the first electrode, and with the second electrode; and
    forming a supporter between the first electrode and the second electrode, the supporter being spaced from the carbon nanotube array.

2. The method of claim 1, wherein the at least one first conductive metal layer has a lower melting point than that of the first electrode, and the at least one second conductive metal layer has a lower melting point than that of the second electrode.

3. The method of claim 1, wherein the at least one first conductive metal layer and the at least one second conductive metal layer are formed by magnetron sputtering process, physical deposition, or chemical vapor deposition.

4. The method of claim 1, wherein the step of electrically connecting each of the carbon nanotubes with the first electrode and with the second electrode comprises:
   heating the at least one first conductive metal layer;
   embedding the first end of each of the carbon nanotubes into the at least one first conductive metal layer;
   heating the at least one second conductive metal layer; and
   embedding the second end of each of the carbon nanotubes into the at least one second conductive metal layer.

5. The method of claim 1, further comprising a step of forming a modified layer on an outer surface of each of the carbon nanotubes before forming the first metallophilic layer and the second metallophilic layer.

6. The method of claim 5, wherein the modified layer comprises a material selected from the group consisting of palladium, platinum, and gold.

7. The method of claim 1, wherein the first metallophilic layer and the second metallophilic layer are formed by electroplating, electroless plating, evaporating plating, or meganetron sputtering.

8. A method for fabricating a carbon nanotube array sensor, the method comprising:
   growing a plurality of carbon nanotubes from a substrate, the carbon nanotubes having first free top ends;
   forming first metallophilic layers on the first free top ends of the carbon nanotubes, the first metallophilic layers comprise a material selected from the group consisting of gold, graphite, palladium, chromium, nickel, titanium, and magnesium;
   providing a first electrode and a second electrode;
   arranging first conductive metal layers on the first free top ends of the carbon nanotubes, the first conductive metal layers having a lower melting point than that of the first electrode;
   heating the first conductive metal layers to soften the first conductive metal layers such that the first free top ends of the carbon nanotubes electrically connect with the first electrode;
   peeling off the substrate from the carbon nanotubes so that second free bottom ends of the carbon nanotubes are exposed;
   forming second metallophilic layers on the second free bottom ends of the carbon nanotubes;
   arranging second conductive metal layers on the second free bottom ends of the carbon nanotubes, the second conductive metal layers having a lower melting point than that of the second electrode;
   heating the second conductive metal layers to soften the second conductive metal layers such that the second free bottom ends of the carbon nanotubes electrically connect with the second electrode; and
   forming a supporter between the first electrode and the second electrode, the supporter being spaced from the carbon nanotube array.

9. The method of claim 8, further providing a supporter attached between the first electrode and the second electrode.

10. The method of claim 8, wherein each of the first free top ends of each of the carbon nanotubes has one of the first metallophilic layers and one of the first conductive metal layers, and each of the second free bottom ends of each of the carbon nanotubes has one of the second metallophilic layers and one of the second conductive metal layers.

11. The method of claim 1, wherein the first metallophilic layer and the second metallophilic layer are wetted with each of the carbon nanotubes, the first metallophilic layer is wetted with the at least one first conductive metal layer, and the second metallophilic layer is wetted with the at least one second conductive metal layer.

12. The method of claim 1, wherein the first metallophilic layer directly contacts and connects with the at least one first conductive metal layer and the second metallophilic layer directly contacts and connects with the at least one second conductive metal layer.

13. The method of claim 1, wherein the supporter is made of an insulating material.

14. The method of claim 13, wherein the insulting material is selected from the group consisting of glass, ceramic, and combinations thereof.

* * * * *